United States Patent
Aumüller et al.

[11] Patent Number: 6,147,145
[45] Date of Patent: Nov. 14, 2000

[54] STABILIZED MONOMER COMPOSITION

[75] Inventors: Alexander Aumüller, Neustadt; Andreas Koch, Bobenheim-Roxheim; Heinz Friedrich Sutoris, Frankenthal; Jacques Dupuis, Ludwigshafen; Manfred Niessner, Schifferstadt, all of Germany

[73] Assignee: BASF Aktiengesellschaft, Ludwigshafen, Germany

[21] Appl. No.: 09/147,003

[22] PCT Filed: Mar. 4, 1997

[86] PCT No.: PCT/EP97/01085

§ 371 Date: Sep. 8, 1998

§ 102(e) Date: Sep. 8, 1998

[87] PCT Pub. No.: WO97/32833

PCT Pub. Date: Sep. 12, 1997

[30] Foreign Application Priority Data

Mar. 9, 1996 [DE] Germany ............ 196 09 312

[51] Int. Cl.$^7$ ...................................... C08K 5/34
[52] U.S. Cl. ................................ 524/86; 524/89
[58] Field of Search ......................... 524/86, 99

[56] References Cited

U.S. PATENT DOCUMENTS

| | | | |
|---|---|---|---|
| 4,670,131 | 6/1987 | Ferrell . | |
| 4,972,009 | 11/1990 | Suhadolnik et al. | 524/99 |
| 4,983,738 | 1/1991 | Kazmierczak et al. | 546/208 |
| 5,254,760 | 10/1993 | Winter et al. | 585/5 |
| 5,396,005 | 3/1995 | Arhancet . | |

FOREIGN PATENT DOCUMENTS

| | | |
|---|---|---|
| 2 084 869 | 12/1971 | France . |
| 0 737 660 | 10/1996 | France . |
| 43 28 950 | 3/1994 | Germany . |
| 44 14 773 | 11/1994 | Germany . |
| 195 19 628 | 12/1995 | Germany . |
| WO 96 29311 | 9/1996 | WIPO . |

OTHER PUBLICATIONS

Thermal Polymerization of Styrene in the Presence of Stable Radicals and Inhibitors Mardare et al. In Polym. Prep. (Am. Chem. Soc., Div. Polym. Sci.) 35 (1), 778 (1994).

*Primary Examiner*—Edward J. Cain
*Attorney, Agent, or Firm*—Oblon, Spivak, McClelland, Maier & Neustadt, P.C.

[57] ABSTRACT

A monomer composition is described, containing

A) vinyl-containing monomers in which the vinyl bears a hetero-atom selected from the group consisting of the halogens, nitrogen, oxygen, sulfur or silicon, and B) at least one N-oxyl compound of a secondary amine which does not bear hydrogen on the α-carbons, in an amount effective as stabilizer against premature polymerization.

17 Claims, No Drawings

STABILIZED MONOMER COMPOSITION

The present invention relates to monomer compositions containing
  A) vinyl-containing monomers in which the vinyl bears a hetero-atom selected from the group consisting of the halogens, nitrogen, oxygen, sulfur or silicon, and
  B) at least one N-oxyl compound of a secondary amine which does not bear hydrogen on the α-carbons, in an amount effective as stabilizer against premature polymerization.

The invention further relates to processes for inhibiting the premature polymerization of vinyl-containing monomers and to the use of N-oxyl compounds of secondary amines which do not bear hydrogen on the α-carbons as stabilizers against premature polymerization.

To prevent premature polymerization, it is necessary to add stabilizers to the monomers. Those which have proved particularly suitable for preventing free-radical polymerizations are sterically hindered amines, such as 2,2,6,6-tetraalkylpiperidine, and their derivatives, including also the N-oxyl derivatives.

U.S. Pat. No. 5,254,760 describes the stabilization of vinylaromatic compounds such as styrene during distillation and purification by a combination of at least one nitroxyl compound and at least one aromatic nitro compound, in which there is the risk that traces of the nitroxyl compounds pass into the purified monomer. Even traces of nitroxyl compounds interfere with the subsequent polymerization, however; they cause delayed polymerization and uncontrolled chain breaks, leading to polymers which are insufficiently reproducible and are of short chain length. These disadvantageous effects are described by Mardare et al. in Polym. Prep. (Am. Chem. Soc., Div. Polym. Sci.) 35 (1), 778 (1994).

To stabilize heterosubstituted vinyl compounds such as N-vinylformamide or N-vinylpyrrolidone, derivatives of phenylenediamine (U.S. Pat. No. 5,396,005), fullerenes (DE-A 44 14 773) or 2,6-di-tert-butyl-p-cresole (DE-A 43 28 950), for example, have previously been used in distillation and purification, but the efficiency of these stabilizers is considered to be inadequate.

It is an object of the present invention, therefore, to find monomer compositions which contain heterosubstituted vinyl compounds and suitable stabilizers, which display improved stabilization against premature polymerization and which have virtually no disadvantageous effects on the following targeted polymerization of the monomers.

We have found that this object is achieved by the monomer compositions mentioned at the outset.

The heterosubstituted vinyl monomers preferably bear, as hetero-atom on the vinyl group, halogens, oxygen, nitrogen or sulfur.

Hetero-substituted vinyl monomers which are suitable are, for example, vinyl halides, such as vinyl chloride, vinyl esters of carboxylic acids, such as vinyl acetate, vinyl propionate or vinyl butyrate, vinyl ethers, such as methyl vinyl ether, ethyl vinyl ether or butyl vinyl ether, vinyl thioethers, vinyl carbazoles, vinyl pyrrolidones, vinyl phthalimides, vinyl isocyanates, vinylcaprolactams, vinylimidazoles, vinylformamide, vinylsulfonic acid and vinylsilanes, such as vinyltriacetoxysilane, vinyltrichlorosilane or vinyltrimethoxysilane.

Preferred monomer compositions contain
A) monomers of the general formula I

where
X is oxygen or —NR²—,
R¹ is

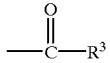

or —R³,

R² is hydrogen, $C_1$–$C_4$-alkyl or, together with R³, is a saturated or unsaturated $C_3$-, $C_4$- or $C_5$-alkylene bridge in which up to two $CH_2$ groups can be replaced by NH, N($C_1$–$C_4$-alkyl), N($C_6$–$C_{10}$-aryl) or oxygen and up to two CH groups can be replaced by N and R³ is hydrogen, $C_1$–$C_4$-alkyl or a radical which, together with R², is a saturated or unsaturated $C_3$-, $C_4$- or $C_5$-alkylene bridge in which up to two $CH_2$ groups can be replaced by NH, N($C_1$–$C_4$-alkyl), N($C_6$–$C_{10}$-aryl) or oxygen and up to two CH groups can be replaced by N, and B) at least one N-oxyl compound of a secondary amine which does not bear hydrogen on the α-carbons in an amount effective as stabilizer against premature polymerization.

The monomers (A) of the general formula I which are present in the mixtures of the invention can contain oxygen as the variable X. Monomers of this type which are particularly suitable as a constituent of the novel monomer compositions are vinyl ethers in which R¹ is $C_1$–$C_4$-alkyl, i.e. methyl, ethyl, n-propyl, isopropyl, n-butyl, isobutyl, sec-butyl or tert-butyl.

If the variable X is —NR²—, R¹ is preferably —CO—R³.

Radicals R³ which are suitable are, in addition to hydrogen and said $C_1$–$C_4$-alkyl groups, those radicals which form, together with —NR²—, a saturated or unsaturated 5- to 7-membered ring, for example:

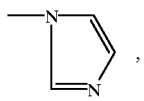

or

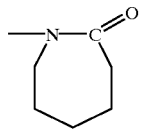

including particularly N-pyrrolidinonyl and N-caprolactamyl.

Preferred monomers in the compositions of the invention are N-vinylformamide, N-vinyl-2-pyrrolidone, N-vinyl-ε-caprolactam and the abovementioned $C_1$–$C_4$-alkyl vinyl ethers.

Particular preference is given among these monomers to N-vinylformamide.

As stabilizers (B), the novel monomer compositions contain at least one N-oxyl compound of a secondary amine which does not bear hydrogen on the α-carbons. These compounds can be present as the free form or as their salts.

Suitable N-oxyls of amines are eg. the following structures

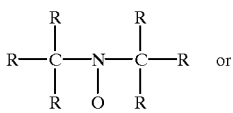 or 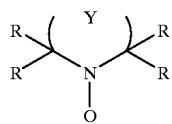

where R is identical or different alkyl, cycloalkyl, aralkyl or aryl, which can also be joined in pairs to form a ring system, and Y is a group which is necessary to complete a 5- or 6-membered ring. R is, for example, $C_1$–$C_{20}$-alkyl, in particular $C_1$–$C_8$-alkyl, $C_5$- or $C_6$-cycloalkyl, benzyl or phenyl. Y is, for example, an alkylene group —(CH$_2$)$_2$— or —(CH$_2$)$_3$—.

Furthermore, N-oxyl compounds are suitable, such as those having the following structures

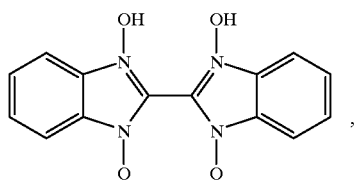,

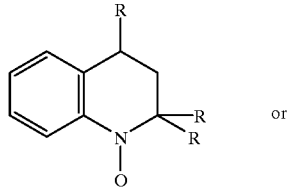 or

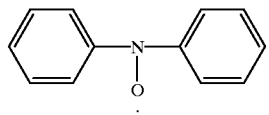

where the aromatic rings can each further bear from 1 to 3 inert substituents, such as $C_1$–$C_4$-alkyl, $C_1$–$C_4$-alkoxy or cyano.

Preferably, sterically hindered cyclic amine derivatives are used, eg. of piperidine or pyrrolidine compounds which can contain a further heteroatom in the ring such as nitrogen, oxygen or sulfur, where this heteroatom is not adjacent to the hindered amine nitrogen. The steric hindrance is due to substituents in the two adjacent positions to the amine nitrogen, suitable substituents being hydrocarbon radicals which replace all 4 hydrogens of the α—CH$_2$ groups. Specific examples of such substituents are phenyl, $C_3$–$C_6$-cycloalkyl, benzyl and, in particular, $C_1$–$C_6$-alkyl, where the alkyl radicals bound to the same α-carbon can also be joined together to form a 5- or 6-membered ring. Particular preference is given to the radicals listed in detail under $R^4$ and $R^5$. Preferably, the N-oxyls of sterically hindered amines used are derivatives of 2,2,6,6-tetraalkylpiperidine.

Preferred N-oxyl compounds in the monomer compositions of the invention are those of the general formula II

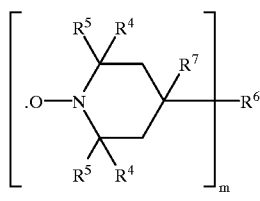

where
$R^4$, $R^5$ are $C_1$–$C_4$-alkyl, phenyl or, together with the carbon to which they are bound, are a 5- or 6-membered saturated hydrocarbon ring,
$R^6$ is hydrogen, hydroxyl, amino or an m-valent organic radical bound by oxygen or nitrogen or, together with $R^7$, is an oxygen or a ring structure defined under $R^7$,
$R^7$ is hydrogen, $C_1$–$C_{12}$-alkyl or, together with $R^6$, is oxygen or together with $R^6$ and the carbon to which they are bound, is the following ring structures

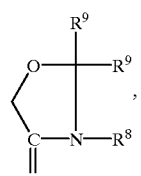, 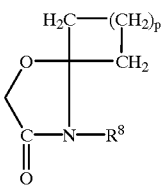

or

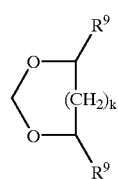

where, for the cases when $R^6$ jointly forms a radical with $R^7$, m=1,
$R^8$ is hydrogen, $C_1$–$C_{12}$-alkyl or —(CH$_2$)$_z$—COOR$^9$,
$R^9$ is identical or different $C_1$–$C_{18}$-alkyl,
k is 0 or 1
z, p are from 1 to 12 and
m is from 1 to 100.

$R^4$ and $R^5$ can be, for example, the $C_1$–$C_4$-alkyl groups mentioned for $R^1$, or they can together form tetramethylene or pentamethylene. Preferably, $R^4$ and $R^5$ are methyl.

Suitable examples of $R^7$ are hydrogen, the abovementioned $C_1$–$C_4$-alkyl groups, and also pentyl, sec-pentyl, tert-pentyl, neopentyl, hexyl, 2-methylpentyl, heptyl, 2-methylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl, (the names isooctyl, isononyl and isodecyl are trivial names and are derived from the carbonyl compounds obtained by oxosynthesis; c.f. in this context Ullmann's Encyclopedia of Industrial Chemistry, 5th Edition, Vol. A1, pages 290–293, and Vol. A10, pages 284 and 285).

p is preferably 6–12, particularly preferably 9.
z is preferably 1–4, particularly preferably 2.
Examples of $R^8$ which are suitable are, in addition to hydrogen, the abovementioned $C_1$–$C_{12}$-alkyl groups. Preferably, $R^8$ is hydrogen, $C_1$–$C_4$-alkyl or (CH$_2$)$_z$—COO($C_1$–$C_6$-alkyl), particularly preferably —CH$_2$—CH$_2$—COO(CH$_2$)$_1$—CH$_3$ and —CH$_2$—CH$_2$—COO(CH$_2$)$_{13}$—CH$_3$.

$R^9$ can be, for example, one of the abovementioned $C_1$–$C_{12}$-alkyl groups or tridecyl, isotridecyl, tetradecyl, pentadecyl, hexadecyl, heptadecyl or octadecyl. Preference is given to dodecyl and hexadecyl.

Examples of preferred radicals $R^6$ are the following m-valent radicals

As $R^{10}$, the same radicals are suitable as are mentioned for $R^8$. Preferably, $R^{10}$ is $C_1$–$C_4$-alkyl.

As $R^{11}$, in addition to hydrogen, the same radicals are suitable as have been mentioned for $R^9$. Preferably, $R^{11}$ is hydrogen.

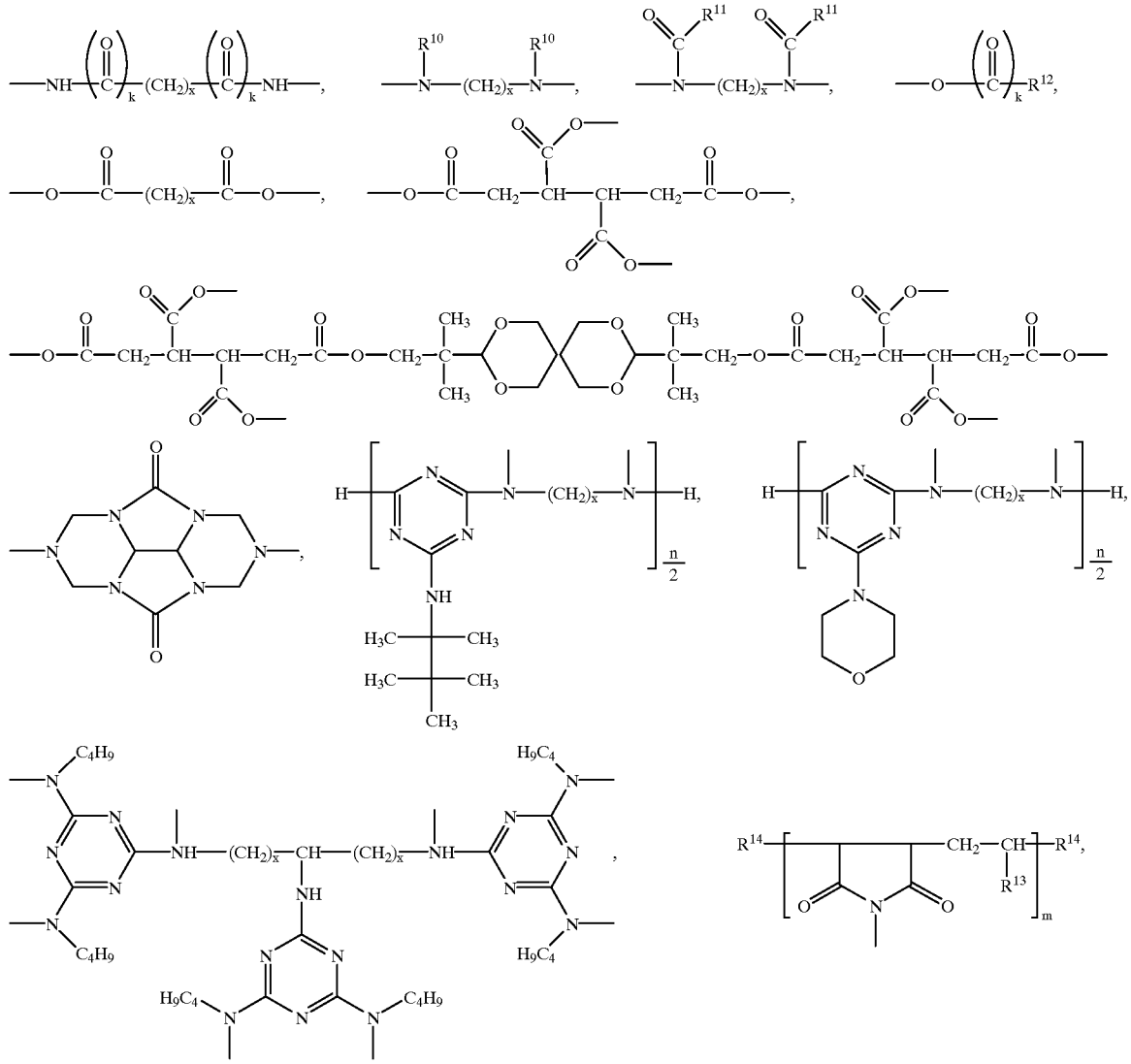

where
- $R^{10}$ is $C_1$–$C_{12}$-alkyl or —$(CH_2)_z$—$COOR^9$
- $R^{11}$ is hydrogen or $C_1$–$C_{18}$-alkyl,
- $R^{12}$ is $C_1$–$C_{18}$-alkyl, vinyl or isopropenyl,
- $R^{13}$ is $C_8$–$C_{22}$-alkyl,
- $R^{14}$ is hydrogen or an organic radical such as is customarily formed in the free-radical polymerization of the starting monomers,
- k is 0 or 1,
- x is from 1 to 12 and
- n is an even number m.

If $R^6$ is one of these radicals, $R^7$ is preferably hydrogen. the variable m in this case can be from 1 to 100, preferably 1,2,3,4 or a number from 10 to 50, mixtures generally being used, particularly in the case of the oligomeric or polymeric radicals $R^6$.

As $R^{12}$, vinyl, isopropenyl or $C_{15}$–$C_{17}$-alkyl are particularly suitable.

Examples of $R^{13}$ which are suitable are the abovementioned $C_8$–$C_{18}$-alkyl radicals and nonadecyl, eicosyl, uneicosyl and doeicosyl, mixtures of various radicals $R^{13}$, which differ in the length of the carbon chain being preferred.

The radicals $R^{14}$ are hydrogen or organic radicals such as are formed in the free-radical polymerization of the starting monomers, in this case from an ethylene derivative and a maleimide derivative, i.e. a radical, for example, which is formed from the polymerization initiator or from a free radical which occurs as an intermediate, or another radical of this type as is customary to those skilled in the art.

Preferred nitroxyl compounds as component B) of the novel monomer compositions are also the following:

1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl (4-tert-butyl) benzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl) adipinamide,
N-(1-oxyl-2,2,6,6-tetramethylpiperidin-4-yl)caprolactam,
N-(1-oxyl-2,2,6,6-tetramethylpiperidin-4-yl) dodecylsuccinimide,
2,4,6-tris-[N-butyl-N-(1-oxyl-2,2,6,6,-tetramethylpiperidin-4-yl]-s-triazine,
4,4'-ethylene-bis(1-oxyl-2,2,6,6-tetramethylpiperazin-3-one) and
tris-(2,2,6,6-tetramethyl-1-oxylpiperidin-4-yl) phosphite.

The nitroxyl compounds described may be prepared from the corresponding piperidine compounds by oxidation, e.g. with hydrogen peroxide. Details of this oxidation are mentioned, for example, in the earlier German Patent Application 195 101 84.7. The secondary amines which do not bear hydrogen on the α-carbons, such as piperidine compounds, and their preparation, are generally known.

Since the oxidation reactions do not always proceed completely, the piperidine compounds acting as starting compounds and partially oxidized intermediates can also be present in the monomer compositions of the invention.

Particularly suitable monomer compositions are those which, apart from the nitroxyl compounds mentioned, additionally contain one or more aromatic nitroso or nitro compounds for stabilization.

Examples of aromatic nitro compounds which can be used are 1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-methylphenol, 2,4-dinitrochloroberzene, 2,4-dinitrophenol, 2,4-dinitro-6-sec-butylphenol, 4-cyano-2-nitrophenol, 3-iodo-4-cyano-5-nitrophenol, particularly preferably 2,6-dinitro-4-methylphenol, 2-nitro-4-methylphenol, 2,4-dinitro-6-sec-butylphenol or. 2,4-dinitro-6-methylphenol.

Suitable aromatic nitroso compounds are, for example, p-nitrosophenol, p-nitroso-o-cresole and p-nitroso-N,N'-diethylaniline.

In addition, substituted phenols can also be added to the monomer compositions as costabilizers, such as for example the following:
4-tert-butylcatechol, methoxyhydroquinone, 2,6-di-tert-butyl-4-methylphenol, n-octadecyl β-(3,5-di-tert-butyl-4-hydroxyphenyl)propionate, 1,1,3-tris-(2-methyl-4-hydroxy-5-tert-butylphenyl)butane, 1,3,5-trimethyl-2,4,6-tris-(3,5-di-tert-butyl-4-hydroxybenzyl)benzene, 3,5-tris-(3,5-di-tert-butyl-4-hydroxybenzyl) isocyanurate,
1,3,5-tris-[β-(3,5-di-tert-butyl-4-hydroxyphenyl) propionyloxyethyl] isocyanurate, 1,3,5-tris-(2,6-dimethyl-3-hydroxy-4-tertbutylbenzyl) isocyanurate and pentaerythritol tetrakis-[β-(3,5-di-tert-butyl-4-hydroxyphenyl)propionate].

Furthermore, the novel monomer compositions may also contain one or more costabilizers selected from the group consisting of phenothiazines, quinones, hydroxylamines or phenylenediamines.

To stabilize the monomer compositions of the invention, these compositions generally contain from 0.0002 to 5, preferably from 0.0005 to 0.5% by weight of the nitroxyl compounds, based on the total amount of the monomer composition.

The stabilizers display their stabilizing action in a broad temperature range, being active at any conventional storage temperature from −50 to +50° C. and likewise at elevated temperatures, as employed, for example, in the distillation of the monomers. The pressure range of the stabilizing process is not critical either. The stabilizers act at atmospheric pressure and also at reduced pressure, as is sometimes employed in distillation processes.

The process of the invention for inhibiting premature polymerization of monomers is used during preparation, distillation or purification of the monomers and also in their storage and transport.

EXAMPLE

Storage of N-vinylformamide in the presence of N,N'-bis (1-oxyl-2,2,6,6-tetramethylpiperidin-4-yl)-N,N'-bis-formyl-1,6-diaminohexane A monomer composition of vinylformamide and 0.05% by weight of N,N'-bis(1-oxyl-2,2,6,6-tetramethylpiperidin-4-yl)-N,N'-bis-formyl-1,6-diaminohexane, based on the total amount of the composition, was stored at 40° C. After the times specified in the table, a sample was withdrawn and the content of vinylformamide was determined by iodometric titration. The iodine values determined are listed in the table as a measure of the respective content of vinylformamide.

| Storage time [days] | Iodine value without stabilizer | Iodine value with stabilizer |
| --- | --- | --- |
| 0 | 98.8 | 98.2 |
| 20 | 89.9 | 92.8 |
| 41 | 80.5 | 87.5 |
| 62 | 71.5 | 81.2 |
| 83 | 62.5 | 75.7 |

What is claimed is:
1. A monomer composition, comprising:
a) vinyl-containing monomers in which the vinyl bears a heteroatom selected from the group consisting of nitrogen, oxygen, sulfur and silicon; and
b) at least one N-oxyl compound of a secondary amine which does not bear hydrogen on the α-carbons, in an amount effective as a stabilizer against premature polymerization.
2. The monomer composition of claim 1, wherein said vinyl-containing monomers have the formula (I):

$$CH_2=CH-X-R^1 \quad (I)$$

wherein

X is oxygen or $-NR^2-$;

$R^1$ is $$-\overset{O}{\underset{\|}{C}}-R^3$$

or $-R^3$;

$R^2$ is hydrogen, $C_1-C_4$-alkyl or, together with $R^3$, is a saturated or unsaturated $C_3-C_4$- or $C_5$-alkylene bridge in which up to two $CH_2$ groups can be replaced by NH, $N(C_1-_4$-alkyl), $N(C_6-C_{10}$-aryl) or oxygen and up to two CH groups can be replaced by N; and $R^3$ is hydrogen, $C_1-_4$-alkyl or a radical which, together with $R^2$, is a saturated or unsaturated $C_3-C_4$- or $C_5$-alkylene bridge in which up to two $CH_2$ groups can be replaced by NH, $N(C_1-C_4$-alkyl), $N(C_6-C_{10}$-aryl) or oxygen and up to two CH groups can be replaced by N.

3. The monomer composition of claim 1, wherein said vinyl-containing monomers are selected from the group consisting of N-vinylformamide, N-vinylpyrrolidone, N-vinylcaprolactam, and $C_1-C_4$-alkyl vinyl ether.

4. The monomer composition of claim 1, wherein the vinyl-containing monomer is N-vinylformamide.

5. The monomer composition of claim 1, wherein the vinyl-containing monomer is vinyl chloride.

6. The monomer composition of claim 1, wherein the at least one N-oxyl compound has the formula (II):

$$\left[ \begin{array}{c} R^5 \quad R^4 \\ O-N \underset{R^5 \quad R^4}{\overset{}{\bigcirc}} R^7 \\ \end{array} \right] \quad (II)$$

wherein $R^4$, each $R^5$ are each $C_1-C_4$-alkyl, phenyl or, together with the carbon to which they are bound, are a 5- or 6-membered saturated hydrocarbon ring;

$R^6$ is hydrogen, hydroxyl, amino or an m-valent organic radical bound by oxygen or nitrogen or, together with $R^7$ is oxygen or a ring structure as defined for $R^7$;

$R^7$ is hydrogen, $C_1-C_{12}$-alkyl or, together with $R^6$, is oxygen or, together with $R^6$ and the carbon to which they are bound, is the following ring structures

[ring structures shown]

wherein when $R^6$ jointly forms a radical with $R^7$, m=1;

$R^8$ is hydrogen, $C_1-C_{12}$-alkyl or $-(CH_2)_z-COOR^9$;

$R^9$ is identical or different $C_1-C_{18}$-alkyl;

k is 0 or 1;

z, p are from 1 to 12; and m is from 1 to 100.

7. The monomer composition of claim 6, where $R^6$ in formula (II) is a radical selected from the group consisting of:

[chemical structures shown]

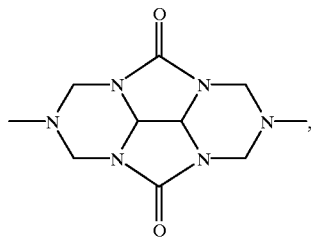
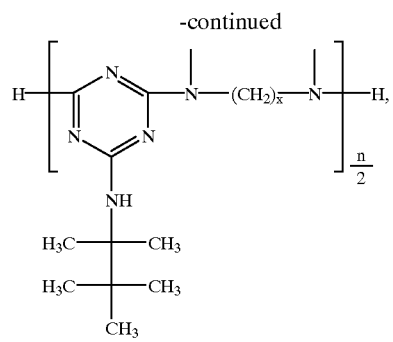
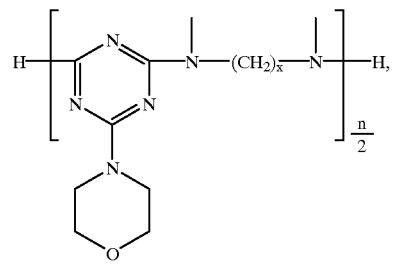
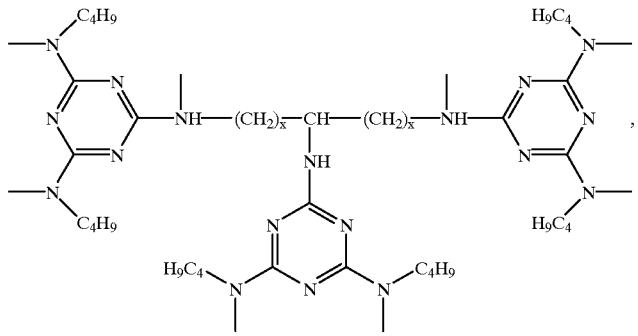
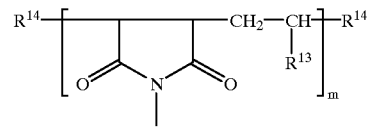

wherein $R^{10}$ is $C_1$–$C_{12}$-alkyl or $(CH_2)_2$—$COOR^9$;

$R^{11}$ is hydrogen or $C_1$–$C_{18}$-alkyl, $R^{12}$ is $C_1$–$C_{18}$-alkyl, vinyl or isopropenyl, $R^{13}$ is a $C_8$–$C_{22}$-alkyl, $R^{14}$ is hydrogen or an organic radical such as is customarily formed in the free-radical polymerization of the starting monomers, k is 0 or 1, x is from 1 to 12 and n is an even number m.

8. The monomer composition of claim 1, which further comprises one or more aromatic nitroso or nitro compounds.

9. The monomer composition of claim 1, which further comprises one or more costabilizers selected from the group consisting of phenothiazines, quinones, hydroquinones and their ethers, hydroxylamines, and phenylene-diamines.

10. The monomer composition of claim 6, wherein $R^8$ is —$CH_2CH_2$—$COO(CH_2)_{11}$—$CH_3$ or —$CH_2CH_2$—$COO(CH_2)_{12}$—$CH_3$.

11. The monomer composition of claim 6, wherein $R^9$ is dodecyl or hexadecyl.

12. The monomer composition of claim 7, wherein $R^{10}$ is $C_1$–$C_4$-alkyl.

13. The monomer composition of claim 7, wherein $R^9$ is hydrogen.

14. The monomer composition of claim 7, wherein $R^{12}$ is vinyl, isopropenyl, or $C_{15}$–$C_{17}$-alkyl.

15. A process for inhibiting the premature polymerization of monomers as claimed in claim 1, which comprises adding at least one N-oxyl compound of a secondary amine which does not bear hydrogen on the α-carbons to the monomers as claimed in claim 14, in an amount effective as stabilizer.

16. The process of claim 15, wherein at least one tetraalkylpiperidine-N-oxyl compound of the formula (II) of claim 19 is added to the monomers.

17. The process of claim 15, wherein the vinyl-containing monomers to be stabilized are selected from the group consisting of N-vinylformide, N-vinylpyrrolidone, N-vinylcaprolactam, and $C_1$–$C_4$-alkyl vinyl ethers.

* * * * *